United States Patent [19]

Jung et al.

[11] Patent Number: 5,527,793
[45] Date of Patent: Jun. 18, 1996

[54] ANTIBIOTIC CARBAPENEM COMPOUNDS

[75] Inventors: Frederic H. Jung, Rilly La Montagne; Jean J. Lohmann, Hermonville, both of France

[73] Assignee: Zeneca Limited, London, United Kingdom

[21] Appl. No.: 86,838

[22] Filed: Jul. 7, 1993

[30] Foreign Application Priority Data

Jul. 21, 1992 [EP] European Pat. Off. ............ 92402103

[51] Int. Cl.$^6$ ...................... A61K 31/395; C07D 487/04
[52] U.S. Cl. ............................................ 514/210; 540/350
[58] Field of Search .................... 540/310, 350; 514/210

[56] References Cited

U.S. PATENT DOCUMENTS

| | | | |
|---|---|---|---|
| 4,206,219 | 6/1980 | Christensen et al. | 424/274 |
| 4,208,422 | 6/1980 | Christensen et al. | 424/274 |
| 4,218,462 | 8/1980 | Christensen et al. | 424/274 |
| 4,232,036 | 11/1980 | Christensen et al. | 424/274 |
| 4,943,569 | 7/1990 | Sunagawa | 514/210 |
| 5,227,376 | 7/1993 | Sunagawa et al. | 514/210 |
| 5,441,949 | 8/1995 | Jung et al. | 514/210 |
| 5,444,057 | 8/1995 | Jung | 514/210 |
| 5,463,046 | 10/1995 | Cho et al. | 540/350 |

FOREIGN PATENT DOCUMENTS

| | | |
|---|---|---|
| 0017992 | 10/1980 | European Pat. Off. . |
| 0126587 | 11/1984 | European Pat. Off. . |
| 0160391 | 11/1985 | European Pat. Off. . |
| 0182213 | 5/1986 | European Pat. Off. . |
| 0243686 | 11/1987 | European Pat. Off. . |
| 0443883 | 8/1991 | European Pat. Off. . |
| 0472062 | 2/1992 | European Pat. Off. . |
| 60-233076 | 11/1985 | Japan . |
| 9217481 | 10/1992 | WIPO . |

*Primary Examiner*—Nicholas Rizzo
*Attorney, Agent, or Firm*—Cushman Darby & Cushman

[57] ABSTRACT

The present invention relates to carbapenems and provides a compound of the formula (I)

$$\text{(I)}$$

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
A is a 5-membered heteroaryl ring containing one nitrogen atom and up to two additional heteroatoms selected from nitrogen, oxygen and sulphur; and is bonded to the nitrogen of the linking carbamoyl group by a carbon atom in the ring, is substituted with the carboxy group on a carbon atom in the ring and is optionally further substituted on a carbon atom in the ring; and
in any ring —NH—, H is optionally replaced by $C_{1-4}$alkyl; or a pharmaceutically acceptable salt or in vivo hydrolysable ester thereof. Processes for their preparation, intermediates in their preparation, their use as therapeutic agents and pharmaceutical compositions containing them are also described.

8 Claims, No Drawings

ANTIBIOTIC CARBAPENEM COMPOUNDS

The present invention relates to carbapenems and in particular to such compounds containing a carboxy substituted 5-membered heterocyclic ring. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first carbapenem, and so far the only, to be commercially marketed is imipenem (N-formimidoyl thienamycin). This compound has a broad spectrum of antibacterial activity.

The present invention provides compounds with a broad spectrum of antibacterial activity including both Gram positive and negative, aerobic and anaerobic bacteria. They exhibit good stability to beta-lactamases. In addition representative compounds of this invention exhibit favourable pharmacokinetics.

The carbapenem derivatives referred to herein are named in accordance with the generally accepted semi-systematic nomenclature:

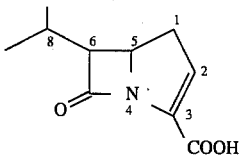

Accordingly the present invention provides a compound of the formula (I)

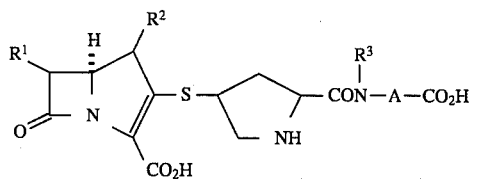

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
A is a 5-membered heteroaryl ring containing one nitrogen atom and up to two additional heteroatoms selected from nitrogen, oxygen and sulphur; and is bonded to the nitrogen of the linking carbamoyl group by a carbon atom in the ring, is substituted with the carboxy group on a carbon atom in the ring, and is optionally further substituted on a carbon atom in the ring, by halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, $C_{1-4}$alkylS(O)$_n$- (wherein n is 0–2), $C_{1-4}$alkanoylamino, $C_{1-4}$alkanoyl(N-$C_{1-4}$alkyl)amino, carbamoyl, $C_{1-4}$alkylcarbamoyl or di-$C_{1-4}$alkylcarbamoyl; and
in any ring —NH—, H is optionally replaced by $C_{1-4}$alkyl; or a pharmaceutically acceptable salt or in vivo hydrolysable ester thereof.

The term alkyl includes all straight and branched chain structures, for example, $C_{1-4}$alkyl includes n-butyl and 2-methylpropyl.

The term heteroaryl means an aromatic ring containing at least one heteroatom in the ring.

Preferably $R^1$ is 1-hydroxyethyl.
$R^2$ is hydrogen or $C_{1-4}$alkyl for example methyl, ethyl, n-propyl, 1-methylethyl and n-butyl.
Preferably $R^2$ is hydrogen or methyl and in particular $R^2$ is methyl.
$R^3$ is hydrogen or $C_{1-4}$alkyl for example methyl, ethyl, n-propyl, 1-methylethyl and n-butyl.
Preferably $R^3$ is hydrogen or methyl.
Most preferably $R^3$ is hydrogen.
Preferably A is thiazole, 1,2,4-thiadiazole, 1,3,4-thiadiazole, oxazole, pyrrole, pyrazole, oxadiazole, imidazole, isoxazole, 1,2,4-thiadiazole or isothiazole. Most preferably A is thiazole, 1,3,4-thiadiazole, pyrrole or imidazole.
Preferably any nitrogen atoms in the heteroaryl ring are unsubstituted.
Suitable substituents for A include, for example:
for halo: fluoro, chloro and bromo;
for $C_{1-4}$alkyl: methyl, ethyl, propyl, 1-methylethyl, butyl and 2-methylpropyl;
for $C_{1-4}$alkoxy: methoxy, ethoxy, propoxy, 1-methylethoxy, butoxy and 2-methylpropoxy;
for $C_{1-4}$alkylcarbamoyl: methylcarbamoyl, ethylcarbamoyl and propylcarbamoyl;
for di-$C_{1-4}$alkylcarbamoyl: dimethylcarbamoyl and diethylcarbamoyl;
for $C_{1-4}$alkylamino: methylamino, ethylamino and propylamino;
for di-$C_{1-4}$alkylamino: dimethylamino, diethylamino and methylethylamino;
for $C_{1-4}$alkylS(O)$_n$-: methylthio, methylsulphinyl and methylsulphonyl;
for $C_{1-4}$alkanoylamino: acetamido and propionamido;
for $C_{1-4}$alkanoyl(N- $C_{1-4}$-alkyl)amino: N-methylacetamido and N-ethylacetamido;
for $C_{1-4}$alkoxycarbonyl: methoxycarbonyl and ethoxycarbonyl.

Preferably, when A is optionally substituted, the optional substituents are selected from halo, cyano, $C_{1-4}$alkyl, nitro, carboxy, hydroxy, $C_{1-4}$alkoxy, carbamoyl, amino and trifluoromethyl.

The present invention covers all epimeric, diastereoisomeric and tautomeric forms of the compounds of the formula (I) wherein the absolute stereochemistry at the 5-position is as illustrated in formula (I). When a bond is represented as a wedge, this indicates that in three dimensions the bond would be coming forward out of the paper and when a bond is represented as hatched, this indicates that in three dimensions the bond would be going back into the paper. The compounds of the formula (I) have a number of other centres of optical activity, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

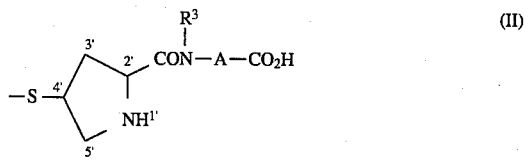

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (III):

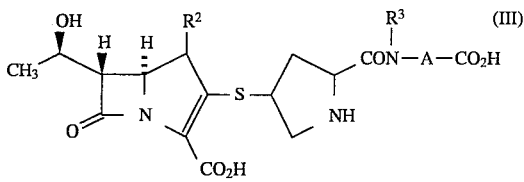

and pharmaceutically acceptable salts and in vivo hydrolysable esters thereof, wherein $R^2$ $R^3$ and optional substituents on the heteroaryl ring are as hereinbefore defined.

When $R^2$ is $C_{1-4}$alkyl for example methyl it is preferred that the compound is in the form of the 1R configuration. Preferred compounds are those in which the pyrrolidine ring has the following absolute stereochemistry at the 2'- and 4'-positions:

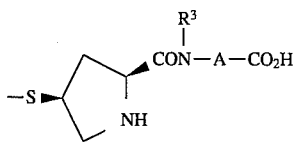

A suitable class of compounds of the present invention is that of the formula (IV):

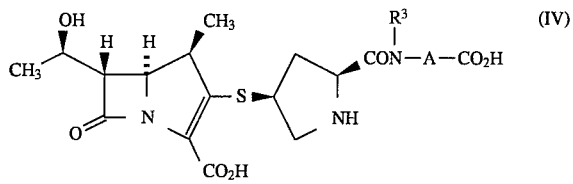

and pharmaceutically acceptable salts and in vivo hydrolysable esters thereof;
wherein A, $R^3$ and optional substituents on A are as defined hereinbefore in formula (I).

In another aspect a suitable class of compounds are the compounds of the formula (IV) wherein $R^3$ is hydrogen, methyl or ethyl; and A and optional substituents on A are as defined hereinabove in formula (I).

In yet another aspect a suitable class of compounds is that of the compounds of the formula (IV) wherein A is optionally further substituted by one or two substituents selected from methyl, ethyl, hydroxy, carboxy, cyano, fluoro, chloro, bromo, carbamoyl, nitro, . methoxy, ethoxy and propoxy; and A and $R^3$ are as defined hereinbefore in formula (I).

A particular class of compounds of the present invention is that of the formula (IV) wherein:
$R^3$ is hydrogen or methyl;
A is as hereinabove defined;
and A is optionally further substituted by one substituent selected from methyl, ethyl, hydroxy, carboxy, cyano, chloro, bromo, nitro, methoxy and ethoxy.

A preferred class of compounds of the present invention is that of the formula (IV) wherein:
$R^3$ is hydrogen;
A is as hereinabove defined;
and A is optionally further substituted by one substituent selected from methyl, hydroxy, chloro and carboxy.

A more preferred class of compounds of the present invention is that of the formula (IV) wherein:

$R^3$ is hydrogen;
A is as hereinabove defined;
and A is not further substituted.

An even more preferred class of compounds of the present invention is that of the formula (IV) wherein:
$R^3$ is hydrogen;
A is thiazole, 1,3,4-thiadiazole, pyrrole or imidazole;
and A is not further substituted.

Particular compounds of the present invention are, for example, the following compounds of the formula (IV):
(1R, 5S,6S,8R,2'S,4'S)-2-(2-(5-carboxythiazol-2-ylcarbamoyl)pyrrolidin -4-ylthio)-6-(1-hydroxyethyl)-1-methylcarbapenem-3-carboxylic acid;

(1R,5S,6S,8R,2'S,4'S)-2-(2-(2-carboxy-1H-imidazol-4-ylcarbamoyl)- pyrrolidin-4-ylthio)-6-(1-hydroxyethyl)-1-methylcarbapenem-3-carboxylic acid;

(1R,5S,6S,8R,2'S,4'S)-2-(2-(2-carboxypyrrol-4-ylcarbamoyl)pyrrolidin- 4-ylthio)-6-(1-hydroxyethyl)-1-methylcarbapenem-3-carboxylic acid;

(1R,5S,6S,8R,2'S 4'S)-2-(2-(4-carboxythiazol-2-ylcarbamoyl)pyrrolidin- 4-ylthio)-6-(1-hydroxyethyl)-1-methylcarbapenem-3-carboxylic acid; and (1R,5S,6S,8R,2'S 4'S)-2-(2-(5-carboxyl-3,4-thiadiazol-2-ylcarbamoyl)-pyrrolidin-4-ylthio)-6-(1-hydroxyethyl)-1-methylcarbapenem-3-carboxylic acid;
and pharmaceutically acceptable salts and in vivo hydrolysable esters thereof.

Suitable pharmaceutically acceptable salts include acid addition salts such as hydrochloride, hydrobromide, titrate, maleate and salts formed with phosphoric and sulfuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or aminoacids, for example, lysine.

Preferred pharmaceutically acceptable salts are sodium and potassium salts. However, to facilitate isolation of the salt during preparation, salts which are less soluble in the chosen solvent may be preferred, whether pharmaceutically acceptable or not.

For the avoidance of doubt there may be one, two, three or four salt-forming cations depending on the number of carboxylic acid functions and valency of said cations.

In vivo hydrolysable esters are those pharmaceutically acceptable esters that hydrolyse in the human body to produce the parent hydroxy or carboxy compound. Such esters can be identified by administering, e.g. intravenously to a test animal, the compound under test and subsequently examining the test animal's body fluids. Suitable in vivo hydrolysable esters for hydroxy include acetoxy, propionyloxy, pivaloyloxy, $C_{1-4}$alkoxycarbonyloxy for example ethoxycarbonyloxy, phenylacetoxy and phthalidyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$cycloalkoxycarbonyloxy$C_{1-6}$alkyl, for example 1-cyclohexyloxycarbonyloxyethyl; 1,3-dioxolen-2-onylmethyl esters for example 5-methyl-1,3-dioxolen-2-onylmethyl; phthalidyl esters and $C_{1-6}$alkoxycarbonyloxyethyl esters for example 1-ethoxycarbonyloxyethyl and may be formed at any carboxy group in the compounds of this invention.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids such as betamipron (also see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable composition containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by any one of examples 2 to 5.

The pharmaceutical compositions of the invention will normally be administered to man in order to combat infections caused by bacteria, in the same general manner as that employed for imipenem due allowance being made in terms of dose levels for the pharmacokinetics of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V) wherein A is optionally further substituted as in formula (I):

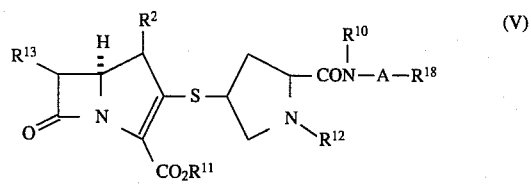

wherein A is as hereinbefore defined; $R^2$ is as hereinbefore defined; $R^{10}$ is a group $R^3$ or an amino protecting group; $R^{13}$ is a group $R^1$, protected hydroxymethyl or 1-(protected hydroxy)ethyl; $R^{11}$ is hydrogen or a carboxy protecting group; $R^{12}$ is hydrogen or an amino protecting group, $R^{18}$ is carboxy or a protected carboxy group and wherein any optional substituent on the heteroaryl ring is optionally protected; and wherein at least one protecting group is present; and thereinafter if necessary;
(i) forming a pharmaceutically acceptable salt,
(ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); diaryl(lower alkyl)silyl groups (e.g. t-butyldiphenylsilyl); and (2-6C)alkenyl groups (e.g. allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxycarbonyl, photolytically.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl); diaryl(lower alkyl)silyl (e.g. t-butyldiphenylsilyl) and aryl lower alkyl (e.g. benzyl) groups.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl); trialkylsilyl (e.g. trimethylsilyl and t-butyldimethylsilyl); diaryl(lower alkyl)silyl (e.g. t-butyldiphenylsily); alkylidene (e.g. methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

In another aspect of the present invention the compounds of the formulae (I) and (V) may be prepared by
a) reacting compounds of the formulae (VI) and (VII):

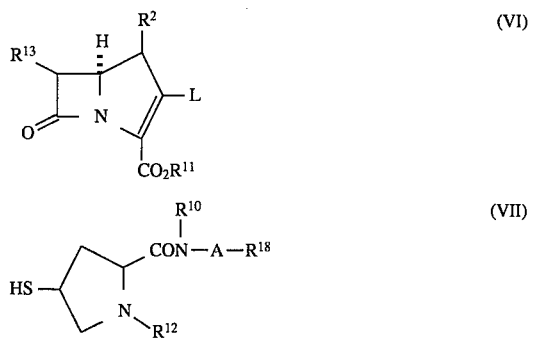

wherein A, $R^2$, $R^{10}$, $R^{11}$, $R^{12}$, $R^{13}$ and $R^{18}$ are as hereinbefore defined optional substitutents on A are as hereinbefore defined and L is a leaving group, or b) cyclising a compound of the formula (VIII):

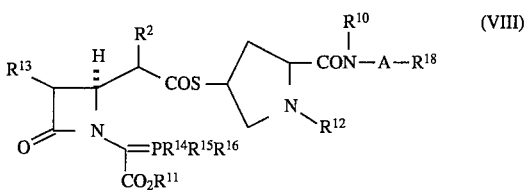

wherein A, $R^2$, $R^{10}$, $R^{11}$, $R^{12}$, $R^{13}$ and $R^{18}$ are as hereinbefore defined, optional substituents on A are as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$–$R^{16}$ represent o-phenylenedioxy or one of $R^{14}$–$R^{16}$ is $C_{1-4}$alkyl, allyl, benzyl or phenyl and the other two values are independently selected from $C_{1-4}$alkyl, trifluoromethyl or phenyl wherein any phenyl-group is optionally substituted with $C_{1-3}$alkyl or $C_{1-3}$alkoxy; and wherein any functional group is optionally protected and thereinafter if necessary:
(i) removing any protecting groups;
(ii) forming a pharmaceutically acceptable salt;
(iii) esterifying to form an in vivo hydrolysable ester.

Suitably in the compound of the formula (VI), L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SOCH=CH—NHCOCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient, suitably at about 0° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

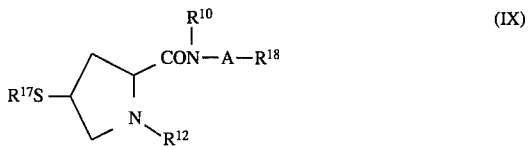

wherein A, $R^{10}$, $R^{12}$ and $R^{18}$ are as hereinbefore defined, optional substitutents on A are as hereinbefore defined and $R^{17}$ is a protecting group, for example $C_{1-6}$alkanoyl or $C_{1-6}$alkoxycarbonyl. Preferred values for $R^{17}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol, alkenol or cyclic ether, for example ethanol, dioxane or tetrahydrofuran.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

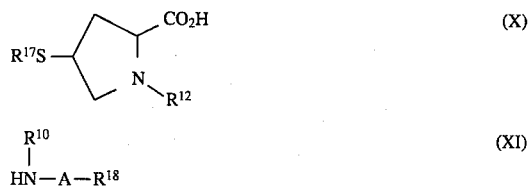

wherein A, $R^{10}$, $R^{12}$, $R^{17}$ and $R^{18}$ are as hereinbefore defined and optional substituents on A are as hereinbefore defined. Activated derivatives of the compound of the formula (X) include acid halides, anhydrides and 'activated' esters such as 1H-benzol-1,2,3-triazol-1-yl, pentafluorophenyl and 2,4,5-trichlorophenyl esters or the benzimidazol-2-yl ester of the thiocarboxylic acid corresponding to (X). The reaction of an activated derivative of a compound of the formula (X) and a compound of the formula (XI) is performed under standard methods, for example in dichloromethane at 4° C. in the presence of diisopropylethylamine or in chloroform at ambient temperature in the presence of N-ethoxycarbonyl-2-ethoxy-1,2-dihydroquinoline.

The compounds of the formulae (X) and (XI) are prepared by standard methods known to the skilled chemist such as the methods of the Examples hereinafter, the methods described in EP-A-126587 or by methods analogous or similar thereto.

Suitably, in the compounds of the formula (VIII), $R^{14}$, $R^{15}$ and $R^{16}$ are independently selected from $C_{1-6}$ alkoxy such as methoxy, ethoxy, isopropoxy, n-propoxy or n-butoxy; aryloxy such as optionally phenoxy; di-$C_{1-6}$alkylamino such as dimethylamino or diethylamino; diarylamino such as diphenylamino or any two of $R^{14}$–$R^{16}$ represent o-phenylenedioxy. Preferably each of $R^{14}$–$R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

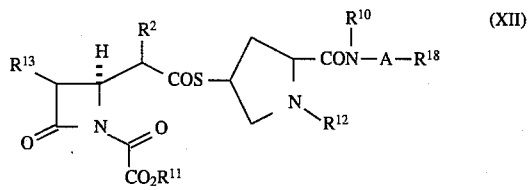

$PR^{14}R^{15}R^{15}$ (XIII)

wherein A, $R^2$, $R^{10}$, $R^{11}$–$R^{16}$ and $R^{18}$ are as hereinbefore defined and optional substituents on A are as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

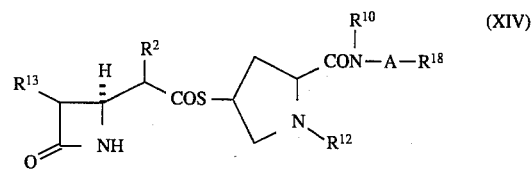

wherein A, $R^2$, $R^{10}$, $R^{12}$, $R^{13}$ and $R^{18}$ are as hereinbefore defined and optional substituents on A are as hereinbefore defined with a compound of the formula (XV):

wherein $R^{11}$ is as hereinbefore defined.

The compounds of the formula (XIV) may be prepared by reacting compounds of the formulae (XVI) and (VII):

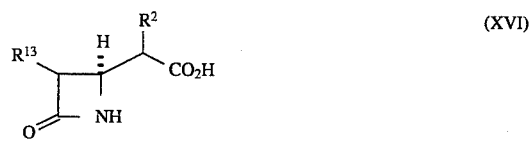

wherein $R^2$ and $R^{13}$ are as hereinbefore defined. The compounds of the formula (XVI) are known in the art and may be reacted with the compounds of the formula (VII) under conventional acylation methods known in the art.

Compounds of the formulae (VII), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and in general particularly good pharmacokinetics, especially as regards half life. In general compounds show significant improvement over imipenem.

The antibacterial properties of the compounds of the invention may also be demonstrated in vivo in convention.. tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| ORGANISM | MIC (μg/ml) EXAMPLE 2 |
| --- | --- |
| S. aureus Oxford | 0.25 |
| E. coli DCO | 0.03 |
| P. morganii I + 001 | 0.03 |
| Enterobacter cloacae P99- | 0.03 |
| B. fragilis AMP S | 0.50 |

In the following examples, which are representative of the scope:
(a) NMR spectra were taken at 200 HHz or 400 HHz in DMSO-$d_6$/CDCOOD unless otherwise stated;
(b) allyloxy means the propen-1-yloxy group —OCH$_2$CH=CH$_2$;
(c) THF means tetrahydrofuran;
(d) DMF means dimethylformamide;
(e) DMSO means dimethylsulphoxide;
(f) EEDQ means N-ethoxycarbonyl-2-ethoxy-1,2-dihydroquinoline
(g) evaporation of solvents was carried out under reduced pressure;
(h) HPLC means high pressure liquid chromatography;
(i) temperatures are in degrees centigrade; and
(j) Heldrum's acid means 2,2-dimethyl-1,3-dioxane-4,6-dione

EXAMPLE 1

(1R,5S,6S,8R,2'S,4'S)-2-(2-(5-Carboxy-2-thiazolylcarbamoyl)pyrrolidin- 4-ylthio)-6-(1-hydroxyethyl)-1-methylcarbapenem-3-carboxylic acid, disodium salt.

To a solution of allyl (1R,5S,6S,8R,2'S,4'S)- 2-(1-(4-nitrobenzyloxycarbonyl)-2-(5-carboxy-2-thiazolylcarbamoyl) pyrrolidin-4-ylthio)-6-(1-hydroxyethyl)-1-methylcarbapenem-3-carboxylate, diisopropylethylamine salt (640 mg; contaminated by an unknown amount of tri-n-butylphosphine) in DMF at 50° C. was added Meldrum's acid (100 mg, 0.7 mmol) followed by tetrakis(triphenylphosphine)palladium (60 mg, 0.05 mmol). The reaction mixture was stirred at 50° C. for 10 minutes, then cooled to ambient temperature and diluted with a solution of 1M phosphate buffer (10 ml). Zinc powder (1 g) was added in small portions over 45 minutes to the stirred solution. After 1 hour, at ambient temperature, the undissolved substances were removed by filtration over diatomaceous earth and the pH of the filtrate adjusted to 8.0 with solid sodium hydrogen carbonate. The reaction mixture was filtered, concentrated under reduced pressure and the resulting residue purified by reverse phase chromatography (Nucleosil C18, 3.5×20 cm), with water as eluant, to give a mixture of the title compound and phosphate buffer after freeze drying. The mixture was purified a second time under the same conditions to give the title compound (72 mg, 30%) as a foam after freeze drying.

NMR: δ 1.16 (d, 3H); 1.18 (d, 3H); 1.76–1.83 (m, 1H); 2.61–2.69 (m, 1H); 2.78–2.83 (m, 1H); 3.20 (dd, 1H); 3.37–3.42 (m, 2H); 3.66–3.70 (m, 1H); 3.95–3.79 (m, 1H); 4.06–4.10 (m, 1H); 4.16 (dd, 1H); 7.97 (s, 1H). MS (+ve FAB): 482 MH$^+$; 527 MH$^+$ Na salt; 550 MH$^+$ diNa salt.

The starting material was prepared as follows:

(2S,4S) 1-(4-Nitrobenzyloxycarbonyl)-2-(5-carboxy-2-thiazolylcarbamoyl) pyrrolidin-4-ylthioacetate. (2S,4S)-1-(4-Nitrobenzyloxycarbonyl)-4-acetylthio-2-carboxypyrrolidine (368 mg, 1 mmol) was solubilized at ambient temperature in thionyl chloride (3 ml). The mixture was stirred for 3 hours at ambient temperature and thionyl chloride evaporated. The residual oil was taken up in toluene, the solvent evaporated and the residue dried under reduced pressure. The crude acid chloride was dissolved in dichloromethane (10 ml) and added dropwise to a solution of ethyl 2-aminothiazol-5-carboxylate (O. Dann, Ber. Dtsch. Chem. Ges. 1943, 76, 419) (172 mg, 1 mmol) and N-ethyldiisopropylamine (0.2 ml, 1.15 mmol) in dichloromethane (10 ml). The reaction mixture was stirred for 2 hours at ambient temperature and overnight at 4° C. After evaporation to dryness, the crude material was purified by subjecting to flash chromatography on silica, eluting with dichloromethane/ethyl acetate (6:4) to give the title compound as a yellow foam (430 mg, 82%). NMR: δ 1.31 (m, 3H); 1.95 (m, 1H); 2.33 (s, 3H); 2.80 (m, 1H); 3.38 (m, 1H); 4.01–4.13 (m, 2H); 4.29 (m, 2H); 4.63 (m, 1H); 5.02–5.30 (m, 2H); 7.43 (d, 1H); 7,65 (d, 1H); 7.96 (d, 1H); 8.11 (d, 1H); 8.23 (d, 1H).

(2S,4S)-1-(4-Nitrobenzyloxycarbonyl)-2-(5-carboxy-2-thiazolylcarbamoyl)pyrrolidin-4 -ylthiol.

(2S,4S)-1-(4-Nitrobenzyloxycarbonyl)-2-(5-carboxy-2-thiazolyl-carbamoyl)pyrrolidin- 4-ylthioacetate was solubilised in a mixture of dioxane/H$_2$O (1/1; 4 ml) and treated with a 2M aqueous solution of NaOH (1.5 ml, 3 mmol). The reaction mixture was stirred for 6 hours at ambient temperature and kept overnight, at 4° C. A 2M aqueous solution of NaOH (0.3 ml, 0.6 mmol) was added to the reaction and stirring continued for 5 hours at ambient temperature. After evaporation to dryness, the crude reaction mixture was dissolved in water and acidified with 1M HCl to pH 4.5. DMF was added to the resulting suspension until a clear solution was obtained. This mixture was further purified by subjecting to chromatography on HP20SS resin with a gradient of acetonitrile (0–60%) in water to give the expected thiol (145 mg, 40%) and a small amount of the corresponding disulfide (35 mg, 10%). NMR: δ 2.00 (m, 1H); 2.79 (m, 1H); 3.24–3.72 (m, 2H); 3.99 (m, 1H); 4.56 (m, 1H); 5.00–5.27 (m, 2H); 7.43 (d, 1H); 7.65 (d, 1H); 7.90–7.97 (m, 2H); 8.23 (d, 1H).

Allyl (1R,5R,6S,8R)-6-(1-hydroxethyl)-1-methyl-2-diphenyl-phosphoryloxycarbapenem-3 -carboxylate was prepared as follows:

To a solution of allyl (1R,5R,6S,8R)-6-(1-hydroxyethyl)-1-methyl-2-oxocarbapenem-3 -carboxylate [prepared in situ from allyl 2-diazo-3-oxo-4-(R)-methyl-4-[(3S,4R)-3-(1-(R)-hydroxyethyl)-2- oxoazetidin-4-yl]-butanoate and rhodium octanoate: see for example EP-A-208889] and di-isopropylethylamine (1.1 equivalents) in acetonitrile, at 0° C., under an argon atmosphere, was added dropwise diphenyl chlorophosphate (1.1 equivalents). The solution was stirred at ambient temperature for 30 minutes to form the corresponding 2-diphenylphosphoryloxycarbapenem.

Allyl (1R,5S,6S,8R,2'S,4'S)-2-(1-(4-nitrobenzyloxycarbonyl)-2-(5- carboxy-2-thiazolylcarbamoyl)pyrrolidin-4-ylthio)-6-(1-hydroxyethyl)-1-methylcarbapenem-3-carboxylate, diisopropylethylamine salt.

To a solution of allyl (1R,5S,6S,8R) 6-(1-hydroxyethyl)-1-methyl-2 -diphenylphosphoryloxycarbapenem-3-carboxylate (250 mg, 0.5 mmol) in DMF (3 ml), at 0° C., were added sequentially diisopropylethylamine (0.21 ml, 1.2 mmol), a solution containing a mixture of (2S,4S)-1-(4-nitrobenzyloxycarbonyl)-2-(5-carboxy-2-thiazol-carbamoyl)pyrrolidin-4 -ylthiol (150 mg, 0.33 mmol) and the corresponding disulfide (45 mg, 0.05 mmol) in DMF (3 ml), tri-n-butylphosphine (0.14 ml, 0.56 mmol) and 2 drops of water. The reaction mixture was stirred for 1 hour at ambient temperature and directly purified by subjecting to chromatography on HP20SS (100 ml) with a gradient of acetonitrile (0–60%) in water. The title compound contaminated with tri-n-butylphosphine eluted between 20% and 45% acetonitrile and was obtained, after lyophilisation, as an orange gum (645 mg). This was used without further purification. NMR: δ 1.17 (m, 6H); 1.27 (m, 14H); 1.90 (m, 1H); 2.82 (m, 1H); 3.14 (q, 2H); 3.26 (dd, 1H); 3.38 (m, 1H); 3.55 (dd, 1H); 3.63 (m, 2H); 3.97–4.24 (m, 3H); 4.58–4.70 (m, 2H); 5.02–5.43 (m, 4H); 5.90 (m, 1H); 7.44 (d, 1H); 7.66 (d, 1H); 7.95-8.02 (m, 2H); 8.23 (d, 1H).

EXAMPLE 2

(1R,5S,6S,8R,2'S,4'S)-2-(2-(4-Carboxy-2-thiazolylcarbamoyl)pyrrolidin- 4-ylthio)-6-(1-hydroxyethyl)71-methylcarbapenem-3-carboxylic acid, disodium salt.

To a solution of allyl (1R,5S,6S,8R,2'S,4'S)-2-(1-nitrobenzyloxycarbonyl)-2-(4-carboxy-2-thiazolylcarbamoyl)pyrrolidin-4-ylthio)-6-( 1-hydroxyethyl)-1-methylcarbapenem-3-carboxylate (250 mg, 0.35 mmol) in DMF (10 ml) was added Heldrum's acid (102 mg, 0.70 mmol) followed by tetrakis(triphenylphosphine)palladium (41 mg, 0.035 mmol). The reaction mixture was stirred at 40° C. for 30 minutes, cooled to ambient temperature and diluted with aqueous solution of 1M phosphate buffer (10 ml). Zinc powder (274 mg, 4.2 mmol) was then added in small portions to the mixture. After 2 hours at ambient temperature, a saturated aqueous solution of sodium hydrogen carbonate was added to the reaction mixture to adjust the pH of the solution to 7.7, the solid filtered off over diatomaceous earth and the filtrate concentrated. The residue was purified by subjecting to reverse phase chromatography (Nucleosil C18, 3.5×20 cm) with acetonitrile in water (0:100 and 4:96) as eluant to give, after freeze drying, the title compound as a white foam (38 mg, 23%). NMR: δ 1.16 (m, 6H); 1.75 (m, 1H); 2.61 (m, 1H); 2.75 (m, 1H); 3.20 (dd, 1H); 3.37 (m, 1H); 3.39 (m, 1H); 3.64 (m, 1H); 3.97 (m, 1H); 4.01 (m, 1H); 4.16 (dd, 1H); 7.92 (s, 1H). MS (-ve FAB): 481MH—

The starting material was prepared as follows:

(2S,4S) 1-(4-Nitrobenzyloxycarbonyl)-2-(4-carbethoxy-2-thiazolyl carbamoyl)pyrrolidin-4-ylthioacetate.

To a solution of (2S,4S)-1-(4-nitrobenzyloxycarbonyl)-4-acetylthio-2-carboxypyrrolidine (4.7 g; 12.8 mmol) in chloroform (250 ml) was added EEDQ (3.5 g; 14 mmol) followed by 2-amino-4-carbethoxythiazole. [J. M. Sprague, R. M. Lincoln and C. Ziegler, J. Amer. Chem. Soc. 68, 266 (1946)] (2.2g, 12.8 mmol). The reaction mixture was stirred at ambient temperature overnight, the solvent evaporated and the residue taken up in DMF (15 ml). This solution was purified by subjecting to chromatography on HP20SS resin, with a gradient of acetonitrile (0–50%) in water. Concentration in vacuo gave an oil which was separated from the aqueous phase, taken up in dichloromethane, dried over $MgSO_4$, filtered and the solvent evaporated to give the title compound as a foam (4.3 g, 65%). NMR: δ 1.30 (t, 3H); 1.95 (m, 1H); 2.80 (m, 1H); 3.40 (m, 1H); 3.95–4.15 (m, 2H); 4.28 (q, 2H); 4.55 (m, 1H); 5.00–5.30 (m, 2H); 7.43 (d, 1H); 7.66 (d, 1H); 7.93 (d, 1H); 8.05 (d, 1H); 8.24 (d, 1H).

(2S,4S)-1-(4-Nitrobenzyloxycarbonyl)-2-(4-carboxy-2-thiazolyl-carbamoyl)pyrrolidin-4 -ylthiol.

To a solution of (2S,4S)-1-(4-nitrobenzyloxycarbonyl)-2-( 4-carbethoxy-2-thiazolylcarbamoyl)pyrrolidin-4-ylthioacetate (3.1 g, 6 mmol) in ethanol (120 ml), at ambient temperature, was added a 1M aqueous solution of sodium hydroxide (22 ml, 22 mmol). After stirring at ambient temperature for 17 hours, ethanol was evaporated, the residue taken up in water (80 ml) and the pH of the solution adjusted to 4.5 with a 1M aqueous solution of hydrochloric acid. The precipitate was filtered off, washed with water, dissolved in DMF (40 ml) and mixed with tri-n-butylphosphine (2 ml) and water (0.8 ml). This mixture was then purified by subjecting to chromatography on HP20SS resin with a gradient of acetonitrile (0–40%) in water. Partial evaporation of the solvents and freeze drying gave the title compound as a white foam (2.06 g, 76%). NMR: δ 1.76 (m, 1H); 2.75 (m, 1H); 3.15–3.59 (m, 2H); 4.00 (m, 1H); 4.50 (m, 1H); 5.03–5.28 (m, 2H); 7.43 (d, 1H); 7.66 (d, 1H); 7.93 (d, 1H); 7.94 (d, 1H); 8.24 (d, 1H).

Allyl (1R,5S,6S,8R,2'S,4'S) 2-(1-(4-nitrobenzyloxycarbonyl 2-(4- carboxy-2-thiazolylcarbamoyl)pyrrolidin-4-ylthio)-6-(1-hydroxyethyl)-1-methylcarbapenem-3-carboxylate.

To a solution of allyl (1R,5S,6S,8R) 6-(1-hydroxyethyl)-1-methyl-2 -diphenylphosphonyloxycarbapenem-3-carboxylate (552 mg, 1.1 mmol) in DMF (16 ml) was added sequentially at 0° C. N-diispropylethylamine (0.46 ml, 2.6 mmol), (2S, 4S)-1-(4-nitrobenzyloxycarbonyl)-2-(4-carboxy- 2-thiazolylcarbamoyl)pyrrolidin-4-ylthiol (500 mg, 1.1 mmol), tri-n-butylphosphine (0.33 ml, 1.3 mmol) and water (0.1 ml). The reaction mixture was stirred at 0° C. for 2.5 hours and purified by subjecting to chromatography on HP20SS resin with a gradient of acetonitrile (0–42%) in water. Partial evaporation of the solvents and freeze drying gave the title compound as a white foam (250 mg, 32%). NMR: δ 1.23 (m, 6H); 1.96 (m, 1H); 2.88 (m, 1H); 3.32 (m, 1H); 3.45 (m, 1H); 3.63 (m, 1H); 4.02–4.06 (m, 2H); 4.25 (m, 1H); 4.31 (m, 1H); 4.60–4.76 (m, 3H); 5.08–5.49 (m, 4H); 5.95 (m, 1H); 7.51 (d, 1H); 7.74 (d, 1H); 8.01 (d, 1H); 8.06 (d, 1H); 8.31 (d, 1H).

EXAMPLE 3

(1R,5S,6S,8R,2,'4'S)-2-(2-(5-Carboxy-1,3,4-thiadiazol-2-carbamoyl) pyrrolidin-4-ylthio)-6-(1-hydroxyethyl)-1-methylcarbapenem-3-carboxylic acid, dipotassium salt.

To a solution containing a 2:1 mixture (700 mg) of allyl (1R,5S,6S,8R,2'S,4'S)-2-(1-(4-nitrobenzyloxycarbonyl)-2-(5-carboxy- 1,3,4-thiadiazol-2-carbamoyl)pyrrolidin-4-ylthio)-6-(1-hydroxy-ethyl)-1-methylcarbapenem-3-carboxylate and an impurity in a mixture of DMF (5 ml) and ethyl acetate (5 ml) were added Meldrum's acid (100 mg, 0.69 mmol) and tetrakis(triphenylphosphine)palladium (40 mg, 0.035 mmol). After 1 hour at ambient temperature, the solvents were evaporated, the residue taken up in water (40 ml) and potassium carbonate (138 mg, 1 mmol) added to the solution. This mixture was washed with ethyl acetate, the aqueous phase mixed with ethyl acetate (40 ml) and 10% palladium on charcoal (300 mg) and stirred under a hydrogen atmosphere (30 psi) at ambient temperature for 1 hour. The reaction mixture was filtered through diatomaceous earth, partially concentrated and purified by subjecting to reverse phase chromatography (Nucleosil C18, 3.5×20 cm) with acetonitrile in water as eluent. The title compound was eluted with water and obtained after freeze drying as a white foam (72 mg, 19%). NMR: δ 1.15 (m, 6H); 1.76 (m, 1H); 2.64 (m, 1H); 2.80 (m, 1H); 3.20 (m, 1H); 3.35–3.41 (m, 2H); 3.67 (m, 1H); 3.97 (m, 1H); 4.07 (m, 1H); 4.16 (m, 1H). The starting material was prepared as follows:

(2S,4S)-1-(4-Nitrobenzyloxycarbonyl)-2-(5-carbethoxy-1,3,4-thiadiazol-2 -carbamoyl)pyrrolidin-4-ylthioacetate.

To a solution of (2S,4S)-1-(4-nitrobenzyloxycarbonyl)-4-acetylthio-2-carboxypyrrolidine (1.83 g, 5 mmol) in chloroform (50 ml) were added EEDQ (1.35 g, 5.5. mmol) and ethyl 2-amino-1,3,4-thiadiazol-5-carboxylate (G. Weber and F Maggio, Ann. Chim. (Rome) 49, 2124 (1959); CA 54 16648d). After 1 hour at ambient temperature the solvent was evaporated, the residue mixed with ethanol (5 ml) and diethyl ether (50 ml) to give the title compound as a crystalline solid (1.90 g, 73%). NMR: δ 1.35 (td, 3H); 1.95 (m, 1H); 2.33 (d, 1H); 2.80 (m, 1H); 3.40 (m, 1H); 3.97–4.11 (m, 2H); 4.40 (q, 2H); 4.64 (m, 1H); 5.00–5.29 (m, 2H); 7.42 (d, 1H); 7.65 (d, 1H); 7.97 (d, 1H); 8.24 (d, 1H).

(2S,4S)-1-(4-Nitrobenzyloxycarbonyl)-2-(5-carboxy-1,3,4-thiadiazol- 2-carbamoyl)pyrrolidin-4-ylthiol.

To a suspension of (2S,4S)-1-(4-nitrobenzyloxycarbonyl)- 2-(5-carbethoxy-1,3,4-thiadiazol-2-carbamoyl)pyrrolidin-4-ylthioacetate in water (2.0 ml) was added, at ambient temperature, a 1M aqueous solution of sodium hydroxide (8 ml). After the addition the reaction mixture was neutralised with acetic acid (0.5 ml) and purified by subjecting to chromatography on HP20SS resin with a gradient of acetonitrile (0.35%) in water. Freeze drying gave the title compound as a foam (0.89 g, 76%). NMR: δ 1.89 (m, 1H); 2.76 (m, 1H); 3.25–3.43 (m, 2H); 4.01 (m, 1H); 4.56 (m, 1H); 5.06–5.25 (m, 2H); 7.44 (d, 1H); 7.66 (d, 1H); 8.01 (d, 1H); 8.24 (d, 1H).

Allyl (1R,5S,6S,8R,2S',4S')-2-(1-(4-nitrobenzyloxycarbonyl)-2-(5- carboxy-1,3,4-thiadiazol-2-carbamoyl)pyrrolidin-4-ylthio)-6-(1-hydroxyethyl)-1-methylcarbapenem-3 -carboxylate.

To a solution of allyl (1R,5S,6S,8R) 6-(1-hydroxyethyl)-1-methyl-2 -diphenylphosphoryloxycarbapenem-3-carboxylate (0.8 g, 1.6 mmol) in DMF (10 ml) was added sequentially, at ambient temperature, N-diisopropylethylamine (1.2 ml, 6.9 mmol), (2S,4S)-1-( 4-nitrobenzyloxycarbonyl)-2-(5-carboxy-1,3,4-thiadiazol-2-carbamoyl) pyrrolidin-4-ylthiol (0.72 g, 1.6 mmol), tri-n-butylphosphine (0.4 ml, 1.6 mmol) and 3 drops water. The reaction mixture was stirred for 2 hours at ambient temperature time and further purified by subjecting to chromatography on HP20SS resin, using a gradient of acetonitrile (0–40%) in water. Freeze drying gave a mixture of the title compound and an impurity. This mixture was used in the deprotection step.

EXAMPLE 4

(1R,5S,6S,8R,2'S,4'S)-2-(2-(2-Carboxy-1H-imidazol-4-ylcarbamoyl)- pyrrolidin-4-ylthio)-6-(1-hydroxyethyl)-1-methylcarbapenem-3-carboxylic acid, disodium salt.

A solution of 4-nitrobenzyl (1R,5S,6S,8R,2'S,4'S)-2-(1-(4 -nitrobenzyloxycarbonyl)-2-(2-carboxy-1H-imidazol-4-yl-carbamoyl)- pyrrolidin-4-ylthio)-6-(1-hydroxyethyl)-1-methylcarbapenem-3-carboxylate, N-diisopropylethylamine salt (300 mg, 0.38 mmol) in a mixture of ethyl acetate (12 ml) and water (12 ml) was mixed with sodium hydrogen carbonate (110 mg, 1.3 mmol) and 10% palladium on charcoal (200 mg). The mixture was stirred under a hydrogen atmosphere (30 psi) for 30 minutes. The catalyst was filtered off, the organic phase discarded and the aqueous phase partially concentrated and purified by subjecting to reverse phase chromatography (Nucleosil C18, 3.5×20 cm) with water as eluant to give, after freeze drying, the title compound (57 mg, 23%). NMR: δ 1.21 (d, 3H); 1.23 (d, 3H); 1.76 (m, 1H); 2.75 (m, 1H); 2.87 (m, 1H); 3.27 (dd, 1H); 3.45 (m, 1H); 3.45 (m, 1H); 3.54 (m, 1H); 3.75 (m, 1H); 4.00–4.10 (m, 2H); 4.22 (dd, 1H); 7.31 (s, 1H). MS (+ve FAB): 460 MH$^+$ The starting material was prepared as follows:

4-Amino-1H-imidazol-2-carboxylic acid

A solution of ethyl 4-amino-1H-imidazol-2-carboxylate (2.0 g, 12.9 mmol) (E. Gomez, C. Avendano and A. McKillop, Tetrahedron 1986, 42, 2635) in ethanol (50 ml) and 1M aqueous sodium hydroxide (14 ml) was refluxed for 20 minutes. The reaction mixture was concentrated to 20 ml and the pH of the solution adjusted to 5 with concentrated hydrogen chloride. The solid which precipitated, collected by filtration and washed with ethanol and ether to give the title compound (1.5 g, 32%). NMR: δ 7.07 (s, 1H).

(2S,4S)-1-(4-Nitrobenzyloxycarbonyl)-2-(2-carboxy-1H-imidazol-4- ylcarbamoyl)pyrrolidin-4-ylthio.

To a solution of (2S,4S)-1-(4-nitrobenzyloxycarbonyl)-4-acetylthio-2-carboxypyrrolidine (1.83 g, 5 mmol) in chloroform (20 ml) was added EEDQ (1.35 g, 5.5 mmol). A solution of 4-amino-1H-imidazol-2-carboxylic acid (0.63 g, 5 mmol) and N-diisopropylethylamine in DMF (5 ml). The reaction mixture was stirred at ambient temperature overnight, the chloroform was evaporated and 1M aqueous sodium hydroxide was added to adjust the pH of the solution to 11.5. After 1 hour at ambient temperature, the solution was acidified to pH 5 with acetic acid. The pure compound was obtained after subjecting to HP20SS resin chromatography with a gradient of acetonitrile (0–50%) in water containing 1% acetic acid and freeze drying (410 mg, 18%). NMR: δ 1.82 (m, 1H); 2.70 (m, 1H); 3.20–3.44 (m, 1H); 3.99 (m, 1H); 4.42 (m, 1H); 5.02–5.28 (m, 2H); 7.37 (s, 1H); 7.76 (d, 1H); 7.66 (d, 1H); 7.95 (d, 1H); 8.27 (d, 1H).

4-Nitrobenzyl (1R,5S,6S,8R,2'S,4'S)-2-(1(4-nitrobenzyloxycarbonyl)-2 -(2-carboxy-1H-imidazol-4-ylcarbamoyl)pyrrolidin-4-ylthio)-6-(1-hydroxylethyl)-1-methylcarbapenem- 3-carboxylate, N,diisopropylethylamine salt.

To a solution of 4-nitrobenzyl (1R,5S,6S,8R)-6-(1-hydroxy- ethyl)-1-methyl-2-diphenylphosphoryloxycarbapenem-3-carboxylate (600 mg, 1 mmol) in DMF (10 ml) was added sequentially, at ambient temperature, N-diisopropylethylamine (0.5 ml, 2.9 mmol) and (2S,4S)-1-(4-nitrobenzyloxycarbonyl)-2- (2-carboxy-1H-imidazol-4-ylcarbamoyl)-pyrrolidin-4-ylthio (400 mg, 0.9 mmol). The reaction mixture was stirred at ambient temperature for 2 hours and purified by subjecting to chromatography on HP20SS resin with a gradient of acetonitrile (0–45%) in water. Partial evaporation of the solvents and freeze drying gave the title compound (300 mg, 38%). NMR: δ 1.17 (d, 3H); 1.18 (d, 3H); 1.24 (m, 9H); 1.84 (m, 1H); 2.78 (m, 1H); 3.13 (q, 2H); 3.25–3.42 (m, 2H); 3.56–3.67 (m, 3H); 3.89–4.03 (m, 2H); 4.09–4.30 (m, 2H); 4.49 (td, 1H); 5.04–5.47 (m, 4H); 7.27 (d, 1H); 7.47 (d, 1H); 7.59 (d, 1H); 7.67 (d, 1H); 7.70 (d, 1H); 7.96 (d, 1H); 8.18–8.26 (m, 3H).

EXAMPLE 5

(1R,5S,6S,8R,2'S,4'S)-2-(2-(2-Carboxy-4-pyrrolylcarbamoyl)pyrrolidin- 4-ylthio)-6-(1-hydroxyethyl)-1-methylcarbapenem-3-carboxylic acid.

A solution of 4-nitrobenzyl (1R,5S,6S,8R,2'S,4'S)-2-(1-(4- nitrobenzyloxycarbonyl)-2-(2-carboxy-4-pyrrolylcarbamoyl)pyrrolidin- 4-ylthio)-6-(1-hydroxyethyl)-1-methylcarbapenem-3-carboxylate (250 mg, 0.32 mmol) in ethyl acetate (10 ml) and water (10 ml) with K₂CO₃ (0.075 g, 0.75 mmol) was hydrogenated at atmospheric pressure with Pd/carbon (10%, 0.2 g), the reaction being followed by HPLC. The mixture was filtered, the filtrate concentrated, and purified by preparative HPLC (C$_{18}$ Nucleosil), eluant water. The required fractions were collected, concentrated and freeze dried to give the title product (84 mg, 48%). NMR: δ 1.15 (2d, 6H); 1.75 (m, 1H); 2.65 (m, 1H); 2.82 (dd, 1H); 3.2 (dd, 1H); 3.3–3.5 (m, 2H); 3.65 (m, 1H); 3.85–4.02 (m, 2H); 4.15 (dd, 1H); 6.78 (s, 1H); 7.24 (s, 1H).

The starting material was prepared as follows:

4-Amino-2-pyrrolecarboxylic acid.

4-Nitro-2-pyrrolecarboxylic acid (0.5 g, 3.2 mmol) in ethanol (10 ml) and water (20 ml) was hydrogenated over Pd/carbon (10%, 100 mg) at atmospheric pressure. After two hours the reaction was over, the catalyst was filtered off over diatomaceous earth, and the ethanol evaporated; the resulting aqueous solution was freeze dried to give the title compound (0.35 g, 88%). NMR (DMSO-d₆) δ 6.13 (s, 1H); 6.28 (s, 1H).

(2S,4S)-1-(4-Nitrobenzyloxycarbonyl)-2-(2-carboxy-4-pyrrolyl- carbamoyl)pyrrolidin-4-ylthioacetate.

(2S,4S)-1-(4-Nitrobenzyloxycarbonyl)-4-acetylthio-2-carboxypyrrolidine (1 g, 2.72 mmol) was solubilized, at ambient temperature, in CH₂Cl₂ (5 ml) in the presence of thionyl chloride (1 ml, 13.7 mmol) and DMF (15 μl ). The mixture was stirred for 4 hours, at ambient temperature, the solvent evaporated, the residual oil dissolved in CH₂Cl₂/toluene 1/1 (10 ml) and evaporated and dried under high vacuum for 1 hour. The residue was then solubilized in CH₂Cl₂ (10 ml). This solution was added to a cold solution (0° C.) of 4-amino-2-pyrrolecarboxylic acid (0.37 g, 2.7 mmol), diisopropylethylamine (1.4 ml, 11.03 mmol) and trimethylsilyl chloride (1.9 ml, 10.93 mmol) in CH₂Cl₂ (anhydrous, 40 ml), and the mixture was stirred at ambient temperature for 2 hours. The solvent was evaporated, the residue dissolved in 2M hydrochloric acid, extracted with ethyl acetate, the organic phase washed with water (three times), dried and filtered to give a solid which was purified by subjecting to HP20SS chromatography (230 ml), using CH₃CN/H₂O/ACOH (50/50/1) as eluant. The required fractions were collected and freeze dried to give the title product (0.6 g, 47%). NMR (DMSO-d₆) δ 1.88 (m, 1H); 2.32 (s, 3H); 2.7 (m, 1H); 3.35 (m, 1H); 3.88–4.12 (m, 2H); 4.38 (m, 1H); 5.0–5.32 (m, 2H); 6.65 (s, 1H); 7.18 (m, 1H); 7.49 (d, 1H); 7.66 (d, 1H); 7.96 (d, 1H); 8.24 (d, 1H).

4-Nitrobenzyl (1R,5R,6S,8R,2'S,4'S)-2-(1-(4-nitrobenzyloxycarbonyl) -2-(2-carboxy-4-pyrrolylcarbamoyl)pyrrolidin-4-ylthio)-6-(1-hydroxyethyl)-1-methylcarbapenem -3-carboxylate.

(2S,4S)-1-(4-Nitrobenzyloxycarbonyl)-2-(2-carboxy-4-pyrrolyl-carbamoyl)pyrrolidin- 4-ylthioacetate (0.33 g, 0.69 mmol) in methanol (20 ml) was treated with (1.15 ml, 1.15 mmol) at ambient temperature. After 1 hour the mixture was evaporated, acidified with 2M hydrochloric acid, saturated with ethyl acetate, washed with water (three times), dried over MgSO₄, filtered and evaporated to give a yellow foam. The crude thiol thus obtained was solubilized in CH₃CN (5 ml) and reacted with 4-nitrobenzyl (1R,5R,6S,8R)-6-(1-hydroxyethyl-1-methyl-2- diphenylphosphoryloxycarbapenem-3-carboxylate (0.4 g, 0,673 mmol) in CH₃CN (5 ml), diisopropylethylamine (0,265 ml, 1.63 mmol), tri-n-butylphosphine (0.035 ml, 0.14 mmol) and water 3 μl, 0.16 mmol) for 1 hour at ambient temperature, overnight at 4° C. The reaction product was purified by subjecting to HP20SS chromatography (100 ml) using CH₃CH/H₂O (40/60) with a gradient of CH₃CN as the eluant, to give the title compound after concentration and freeze drying of the required fractions. (0.26 g, 50%). NMR: δ 1.81 (2d, 6H); 1.88 (m, 1H); 3.4 (m, 1H); 3.85–4.07 (m, 2H); 4.21 (m, 1H); 4.5–4.6 (m, 2H); 4.6–5.12 (m, 2H); 5.7 (d, 1H); 5.8–5.98 (m, 3H); 6.05 (d, 1H); 7.31 (s, 1H); 7.85 (m, 1H); 8.12 (d, 1H); 8.25–8.39 (m, 3H); 8.58 (d, 1H); 8.78–8.91 (m, 3H).

We claim:

1. A compound of the formula (I):

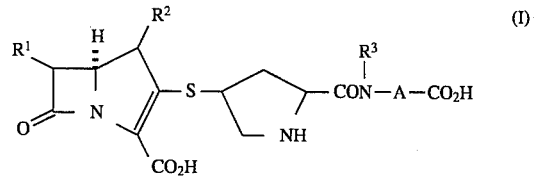

wherein:

R¹ is 1-hydroxyethyl, 1-fluoroethyl or hydroxymethyl;

R² is hydrogen or C$_{1-4}$alkyl;

R³ is hydrogen or C$_{1-4}$alkyl;

A is a 5-membered heteroaryl ring containing one nitrogen atom and up to two additional heteroatoms selected from nitrogen, oxygen and sulphur; and is bonded to the nitrogen of the linking carbamoyl group by a carbon atom in the ring, is substituted with the carboxy group on a carbon atom in the ring and is optionally further substituted on a carbon atom in the ring by halo, cyano, C$_{1-4}$alkyl, nitro, hydroxy, carboxy, C$_{1-4}$alkoxy, trifluoromethyl, C$_{1-4}$alkoxycarbonyl, amino, C$_{1-4}$alkylamino, di-C$_{1-4}$alkylamino, C1-4alkylS(O)$_n$- (wherein n is 0–2), C$_{1-4}$alkanoylamino, C$_{1-4}$alkanoyl(N-C$_{1-4}$alkyl)amino, carbamoyl, C$_{1-4}$alkylcarbamoyl or di-C$_{1-4}$alkylcarbamoyl; and in any ring —NH—, H is optionally replaced by C$_{1-4}$alkyl; or a pharmaceutically acceptable salt or in vivo hydrolysable ester thereof, 2. A compound according to claim 1 wherein R² is methyl.

3. A compound according to claim 1 wherein R¹ is 1-hydroxyethyl.

4. A compound according to either claim 1 or claim 2 of the formula (IV):

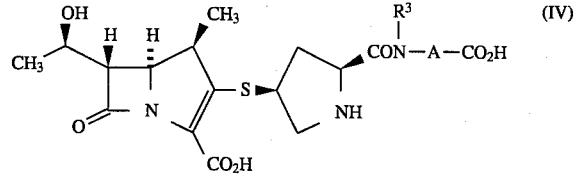

wherein A, R³ and optional substituents on A are as defined in claim 1.

5. A compound according to claim 4 wherein optional substituents on A are selected from halo, cyano, C$_{1-4}$alkyl, nitro, hydroxy, carboxy, C$_{1-4}$alkoxy, carbamoyl, amino and trifluoromethyl.

6. A compound according to claim 1 which is (1R,5S,6S,8R,2'S,4'S)-2-(2-(5-carboxythiazol-2-ylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(2-carboxy-1H-imidazol-4-ylcarbamoyl)- pyrrolidin-4-ylthio)-6-(1-hydroxyethyl)-1-methylcarbapenem-3-carboxylic acid;

(1R,5S,6S,8R,2'S,4'S)-2-(2-(2-carboxypyrrol-4-ylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(4-carboxythiazol-2-ylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(5-carboxy-1,3,4-thiadiazol-2-ylcarbamoyl)pyrrolidin-4-ylthio)-6-(1-hydroxyethyl)-1-methylcarbapenem-3carboxylic acid;

and pharmaceutically acceptable salt thereof.

7. A pharmaceutical composition which comprises a compound according to claim 1 and a pharmaceutically acceptable carrier.

8. A method of treatment of an infection by administering an antibacterially effective amount of a compound of the formula (I) to a patient in need thereof.

* * * * *